United States Patent [19]

Goel

[11] Patent Number: 4,508,653

[45] Date of Patent: Apr. 2, 1985

[54] METHOD FOR PREPARING ACYLOXY STYRENES

[75] Inventor: Anil B. Goel, Worthington, Ohio

[73] Assignee: Ashland Oil, Inc., Ashland, Ky.

[21] Appl. No.: 474,775

[22] Filed: Mar. 14, 1983

[51] Int. Cl.$^3$ .................... C07F 5/08; C07C 67/055
[52] U.S. Cl. .................................. 260/410.5; 560/243
[58] Field of Search ............................ 260/410, 410.5; 560/221, 243, 254

[56] References Cited

U.S. PATENT DOCUMENTS 3,651,127  3/1972  Hornig et al. ...................... 568/802

OTHER PUBLICATIONS

Cram et al., "Organic Chemistry", 2nd ed., (1965) p. 541.

Primary Examiner—Anton H. Sutto
Attorney, Agent, or Firm—John F. Jones

[57] ABSTRACT

The oxidation process for the manufacture of acyloxy styrenes comprises contacting a compound such as styrene or ethyl benzene, a carboxylic acid and molecular oxygen in the liquid phase at an elevated temperature with a catalyst composed of palladium or a compound of palladium, and a compound of at least one member selected from the group consisting of antimony, lead, cobalt, nickel, iron, copper, zinc, chromium, tin and optionally also an alkali metal compound is described.

18 Claims, No Drawings

METHOD FOR PREPARING ACYLOXY STYRENES

This invention relates to the production of acyloxy styrenes and more particularly pertains to a catalytic process for the production of acyloxy styrene, and acyloxy alpha-methyl styrene by reaction of styrene, ethylbenzene, alpha-methyl styrene or cumene with molecular oxygen and a carboxylic acid in the presence of a catalyst comprising palladium or a compound of palladium in conjunction with compounds of certain other metals described below.

In the prior art the palladium catalyzed oxidation of ethyl benzene in acetic acid to produce alpha-methyl benzyl acetate has been described in U.S. Pat. No. 3,547,982. The stoichiometric reaction between styrene and $PdCl_2$ to give some 2-phenylvinyl acetate has been described in *Zb. Pr. Chemickotechnol. Fak. SVST,* 1973-1974, 195-200. There is no other known previous disclosure in the art of the formation of acyloxy styrene from styrene or ethyl benzene using a palladium type catalyst.

I have discovered a process for the production of acyloxy styrene and certain acyloxy substituted styrenes such as acyloxy alpha-methyl styrene by the oxidation of ethyl benzene or styrene over a palladium based catalyst in the presence of a carboxylic acid and in the presence of molecular oxygen. Thus, in my process the starting materials can be ethyl benzene, styrene, cumene or alpha-methyl styrene and the case in which ethyl benzene or styrene is used, the products can be PhCH=CHOCOR, PhC(OCOR)=CH$_2$ and PhC(OCOR)=CHOCOR wherein R is a hydrocarbon group having from 1 to 19 carbon atoms. In the case in which cumene or alpha-methyl styrene is used as the starting material the products can be PhC(CH$_3$)=CHOCOR, PhC(CH$_2$OCOR)=CH$_2$ and PhC(CH$_2$OCOR)=CHOCOR. In the foregoing formulas Ph is a phenyl group and R has the previously mentioned designation. During the oxidation reaction the by-product water is preferably removed from the reaction mixture continuously.

The acyloxy styrenes of my invention and their hydrolysis products are useful monomers for copolymerization with other vinyl monomers, see *J. Polymer Science*, 5, Part A-1, 2655-2664 (1967). The acyloxy styrenes can be hydrolyzed to form hydroxy styrenes by known means or they can be converted to hydroxy-containing polymers by hydrolysis of their ester groups after they have been polymerized.

The palladium based catalyst useful in my process is composed of a palladium compound such as palladium acetate and a compound of at least one member selected from the group consisting of antimony, lead, cobalt, nickel, iron, copper, zinc, chromium and tin. Optionally the catalyst also may contain an alkali metal compound. The catalyst can also optionally contain ligands such as amines, nitriles, phosphines, and the like.

In the process of this invention styrene, or ethyl benzene, for instance, is contacted with oxygen, air, or some other source of molecular oxygen in the liquid phase with a carboxylic acid and with the palladium based catalyst described above at a temperature in the range of from about 100° C. to 300° C., preferably in the range of from about 110°-200° C. The water generated in the process of my invention preferably is removed continuously as it forms preferably by azeotropic distillation with excess ethyl benzene or styrene or with an inert organic solvent or by reaction with an acid anhydride. The inert organic solvent if used can be either a linear aliphatic hydrocarbon having the formula $C_nH_{2n+2}$ wherein n is 5 to 16 or a cyclic aliphatic hydrocarbon having the formula $C_nH_{2n}$ wherein n is 5 to 10.

As the substrate (ethyl benzene or styrene for instance) originally present in the reaction mixture is converted to acyloxy styrene more substrate is ordinarily fed to the reaction mixture.

The catalysts of this invention may be used alone or may be supported on a carrier or support material. Suitable carriers include silica, alumina, carbon, quartz, pumice, diatomaceous earth, and the like, and others which are known in the art.

The carboxylic acids useful in our invention include mono and poly-carboxylic acids having the formula $R(COOH)_n$ wherein n is an integer of from 1 to 2 and R is a hydrocarbon group having at least from 1 to 19 carbon atoms. Most preferred are monocarboxylic acids in which n is 1 and R is an aliphatic hydrocarbon group having from 1 to 19 carbon atoms. Some carboxylic acid anhydride can be included with the carboxylic acid in the reaction if desired.

The process of this invention is further illustrated in the following examples.

EXAMPLE 1

A glass reactor was equipped with a mechanical stirrer, a thermometer with temperature controller unit, a Dean-Stark collector tube to remove water and an assembly to feed organic substrate continuously or intermittantly into the reaction mixture. The reactor was charged with 55.6g (278 millimols) of lauric acid, 1.35 g (6 millimols) of Pd(OAc)$_2$, 2.13 g (7 millimols) of Sb(OAc)$_3$, and 5 ml (43 millimols) of styrene. The reaction mixture was heated, the reaction temperature was maintained at 165°-170° C. and oxygen was bubbled continuously through the reaction mixture at a rate of 30 cc/min. The water produced as a by-product in the reaction was removed by azeotropic distillation with styrene and was collected in the Dean-Stark collector which had been filled with styrene before starting the reaction. As water collected in the Dean-Stark collector it replaced some of the styrene which in turn was introduced into the reactor. Additional styrene was added to the reactor during the course of the reaction. The reaction time was 5 hours during which 25 ml of additional styrene were added making a total of styrene used 30 ml or 261 millimols. At the end of the reaction the product mixture was found by GLC analysis to contain 86 millimols of mono-lauraloxy styrene (PhCH=CHOCOR wherein R is a straight chain aliphatic hydrocarbon radical having 11 carbon atoms) and 4 millimols of di-lauraloxy styrene PhC(OCOR)=CHOCOR wherein R is $C_{11}H_{23}$.

EXAMPLE 2

The procedure of Example 1 was repeated except that in place of styrene there was used 29 ml (237 millimols) of ethyl benzene and the reaction was carried out at 168°-171° C. GLC analysis of the product showed that about 20% of the ethyl benzene was converted to give lauraloxy styrene and alpha methyl benzyl laurate in about 4:1 ratio by weight.

EXAMPLE 3

A glass reactor which was equipped with a mechanical stirrer, a thermometer with a temperature controller unit, a Dean-Stark type collector to remove water and an assembly for feeding the organic substrate continuously or intermittantly into the reaction mixture was used. The reactor was charged with 217 g (1.5 mols) of octanoic acid, 1.68 g (7.5 millimols) of Pd(OAc)$_2$, 2.24 g (7.5 m mols) of Sb(OAc)$_3$, 0.74 g (7.5 m mols) of KOAc, 23.6 g (200 m mols) of alpha-methyl styrene and 20 ml of n-heptane. The Dean-Stark collector was filled with heptane. The reaction mixture was maintained at 165°–170° C. and oxygen was bubbled through the reaction mixture continuously at a rate of 100 cc/min. The water produced as a by-product of the reaction was removed as it formed by azeotropic distillation of the n-heptane and alpha-methyl styrene and was collected in the Dean-Stark collector. Some additional alpha-methyl styrene was added to the reactor occasionally by feed pump. The total reaction time was 5 hours during which 35.4 g (300 m mols) of additional alpha-methyl styrene were added making a total of 500 m mols. At the end of the reaction time the product mixture was found by GLC analysis to contain 260 m mols of 2-phenyl allyl octanoate [PhC(CH$_2$OCOR)=CH$_2$] and 15 m mols of the other isomeric forms such as PhC(CH$_3$)=CHOCOR wherein R is an aliphatic hydrocarbon group having 7 carbon atoms.

EXAMPLE 4

The procedure of Example 3 was followed except that the initial charge to the reactor was composed of 3.19 g (14.2 m mols) of Pd(OAc)$_2$, 5.40 g (14.2 m mols) of Pb(OAc)$_2$.3H$_2$O, 205 g (1420 m mols) of octanoic acid and 24 g (203 m mols) of alpha-methyl styrene, and about 10 ml of n-heptane. The reaction was carried out at 165°–170° C. for 7 hours during which time an additional 35 g (297 m mols) of alpha-methyl styrene were added to the reaction mixture. The GLC analysis of the final reaction mixture showed the formation of 120 m mols of 2-phenyl allyl octanoate and about 11 m mols of the other isomers such as PhC(CH$_3$)=CH OCOR wherein R is C$_7$H$_{15}$.

EXAMPLE 5

The procedure of Example 3 was followed except that the reaction mixture was made up of 0.75 m mols of Pd(OAc)$_2$, 0.75 m mols of Co(OAc)$_2$.4H$_2$O, 300 m mols of octanoic acid and 85 m mols of alpha-methyl styrene. The reaction was carried out at 170° C. for 3 hours to produce 11 m mols of 2-phenyl allyl octanoate and other isomers. Some acetophenone (about 7 m mols) was also produced.

EXAMPLE 6

The procedure of Example 3 was followed except that the catalyst was composed of 0.75 m mols of Pd(OAc)$_2$, 0.75 m mols of Sb(OAc)$_3$ and 0.75 m mols of Cr(OAc)$_3$.H$_2$O. The reaction was carried out at 165°–170° C. for 3 hours during which time 25 m mols of 2-phenyl allyl octanoate and 4 mols of the two other isomers were produced.

EXAMPLE 7

The procedure of Example 3 was followed using in the reaction mixture 3 m mols of Pd(OAc)$_2$, 3 m mols of Sb(OAc)$_3$, 3 m mols of KOAC, 300 m mols of octanoic acid and 83 m mols of cumene. The reaction was carried out at 165°–170° C. for 3 hours during which time 14 m mols of 2-phenyl allyl octanoate and 2 m mols of PhC(CH$_3$)=CHOC)OC$_7$H$_{15}$ were produced.

EXAMPLE 8

The procedure of Example 3 was followed except that the reaction mixture was made up of 20 g (333 m mols) of acetic acid, 20 g (196 m mols) of acetic anhydride, 0.45 g (2 m mols) of Pd(OAc)$_2$, 1.2 g (4 m mols) of Sb(OAc)$_3$, 0.2 g (2 m mols) of KOAc and 14 g (203 m mols) of alpha-methyl styrene. The reaction was carried out for 2½ hours at 126°±2° C. GLC analysis showed the formation of about 11% by weight of 2-phenyl allyl acetate [PhC(CH$_2$OCOCH$_3$)=CH$_2$] and 2.6% by weight of PhC(CH$_3$)=CHOCOCH$_3$. A small amount (about 0.4% by weight) of PhC(CH$_2$OCOCH$_3$)=CHOCOCH$_3$ was also produced. The 2-phenyl allyl acetate was distilled in vacuo (85°–88° C. at 0.7–0.8 mm of Hg.)

EXAMPLE 9

The procedure of Example 8 was repeated except that 18.2 g (175 m mols) of styrene was used in place of the alpha-methyl styrene. The reaction was carried out at about 120° C. for 3½ hours and the resulting mixture was found by GLC analysis to contain 5% by weight of monoacetoxy styrene and 8% by weight of diacetoxy styrene.

EXAMPLE 10

The procedure of Example 3 was followed using a reaction mixture composed of 20 g (270 m mols) of propionic acid, 20 g (154 m mols) of propionic anhydride, 0.45 g (2 m mols) of Pd(OAc)$_2$, 1.2 g (4 m mols) of Sb(OAc)$_3$, 0.2 g (2 m mols) of KOAc and 18.2 g (154 m mols) of alpha-methyl styrene. The reaction was carried out at 145°±3° C. for 3 hours. The GLC analysis showed the formation of about 26% by weight of 2-phenyl allyl propionate and about 3% by weight of PhC(CH$_3$)=CHOCOC$_2$H$_5$. A small amount (about 2%) of the diacyloxylation product was also detected. The colorless liquid 2-phenyl allyl propionate was distilled under 0.1 mm Hg at 86°–88° C.

EXAMPLE 11

The procedure of Example 10 was repeated except that 40 g of propionic acid was used and no propionic anhydride was included in the reaction mixture. After a 3 hour reaction time GLC analysis showed that 18% by weight of 2-phenyl allyl propionate had formed.

EXAMPLE 12

The procedure of Example 11 was repeated except that the Sb(OAc)$_3$ was replaced by an equivalent molar amount of Fe(OAc)$_2$. About 2% by weight of 2-phenyl allyl propionate was formed in the reaction.

I claim:

1. The oxidation process for preparing acyloxy styrene compounds which comprises contacting at least one substrate member selected from the group consisting of styrene, ethyl, benzene, alpha methyl styrene and cumene with a carboxylic acid and molecular oxygen in the liquid phase at a temperature in the range of from about 100° to 300° C. in the presence of a catalyst composed of palladium or a compound of palladium and a compound of at least one member selected from the group consisting of antimony, lead, cobalt, nickel, iron, copper, zinc, chromium, tin and optionally an alkali metal also compound.

2. The process of claim 1 wherein the carboxylic acid is one which corresponds to the formula $R(COOH)_n$ wherein n is an integer of from 1 to 2 and R is a hydrocarbon group having from 1 to 19 carbon atoms.

3. The process of claim 2 wherein n is 1 and R is an aliphatic hydrocarbon group having from 1 to 11 carbon atoms.

4. The process of claim 3 wherein the water formed in the oxidation reaction is continuously removed from the reaction mixture by continuous distillation from the reaction mixture.

5. The process of claim 4 wherein the carboxylic acid is lauric acid.

6. The process of claim 4 wherein the carboxylic acid is octanoic acid.

7. The process of claim 5 wherein the catalyst is composed of $Pd(OAc)_2$ and $Sb(OAc)_3$.

8. The process of claim 6 wherein the catalyst is composed of $Pd(OAc)_2$, $Sb(OAc)_3$ and KOAC.

9. The process of claim 6 wherein the catalyst is composed of $Pd(OAc)_2$ and $Pb(OAc)_2$.

10. The process of claim 6 wherein the catalyst is composed of $Pd(OAc)_2$ and $Co(OAc)_2$.

11. The process of claim 6 wherein the catalyst is composed of $Pd(OAc)_2$, $Sb(OAc)_3$ and $Cr(OAc)_3$.

12. The process of claim 7 wherein the substrate is styrene.

13. The process of claim 7 wherein the substrate is ethyl benzene.

14. The process of claim 8 wherein the substrate is alpha-methyl styrene.

15. The process of claim 9 wherein the substrate is alpha-methyl styrene.

16. The process of claim 10 wherein the substrate is alpha-methyl styrene.

17. The process of claim 11 wherein the substrate is alpha-methyl styrene.

18. The process of claim 8 wherein the substrate is cumene.

* * * * *